United States Patent [19]

Wintrich et al.

[11] Patent Number: 5,668,367
[45] Date of Patent: Sep. 16, 1997

[54] OPTICAL SPACE MONITORING APPARATUS COMPRISING LIGHT GUIDING FIBERS TRANSMITTING LIGHT THROUGH THE SPACE TO BE MONITORED

[75] Inventors: Franz Wintrich; Hartmut Wintrich, both of Essen, Germany

[73] Assignee: BFI Entsorgungstechnologie GmbH, Ratingen, Germany

[21] Appl. No.: 496,846

[22] Filed: Jun. 27, 1995

[51] Int. Cl.$^6$ ......................................................... H01J 5/16
[52] U.S. Cl. ........................................ 250/227.2; 385/116
[58] Field of Search ........................ 250/227.2, 227.22, 250/227.28–227.3; 385/12, 116, 89; 356/32–35, 328, 425, 409–412

[56] References Cited

U.S. PATENT DOCUMENTS

| 3,937,952 | 2/1976 | Ripley et al. | 250/227.22 |
| 4,375,919 | 3/1983 | Busch | 356/328 |
| 4,480,183 | 10/1984 | Ely et al. | 250/227.22 |
| 4,607,963 | 8/1986 | Ulrickson | 374/131 |
| 4,827,143 | 5/1989 | Munakata et al. | 250/227.28 |
| 4,952,022 | 8/1990 | Genovese | 385/116 |
| 4,975,729 | 12/1990 | Gordon | 250/227.28 |
| 5,086,220 | 2/1992 | Berthold et al. | 250/227.2 |
| 5,142,139 | 8/1992 | Hayashi et al. | 250/227.2 |

FOREIGN PATENT DOCUMENTS

| 0 168 235 | 7/1985 | European Pat. Off. . |
| 0 333 493 | 3/1989 | European Pat. Off. . |

OTHER PUBLICATIONS

Patent Abstracts of Japan vol. 007 No. 220 (P–226), 30 Sep. 1983 & JP–A–58 113729 (Tokyo Shibaura Denki KK) 6 Jul. 1983.

Primary Examiner—Que Le
Attorney, Agent, or Firm—Townsend and Townsend and Crew LLP

[57] ABSTRACT

An apparatus for optically monitoring a space, the apparatus including light guiding fibers for transmitting received radiation to a sensor device. The light inlets are arranged in an array while the sensors are arranged in a row which is read out in parallel fashion.

2 Claims, 3 Drawing Sheets

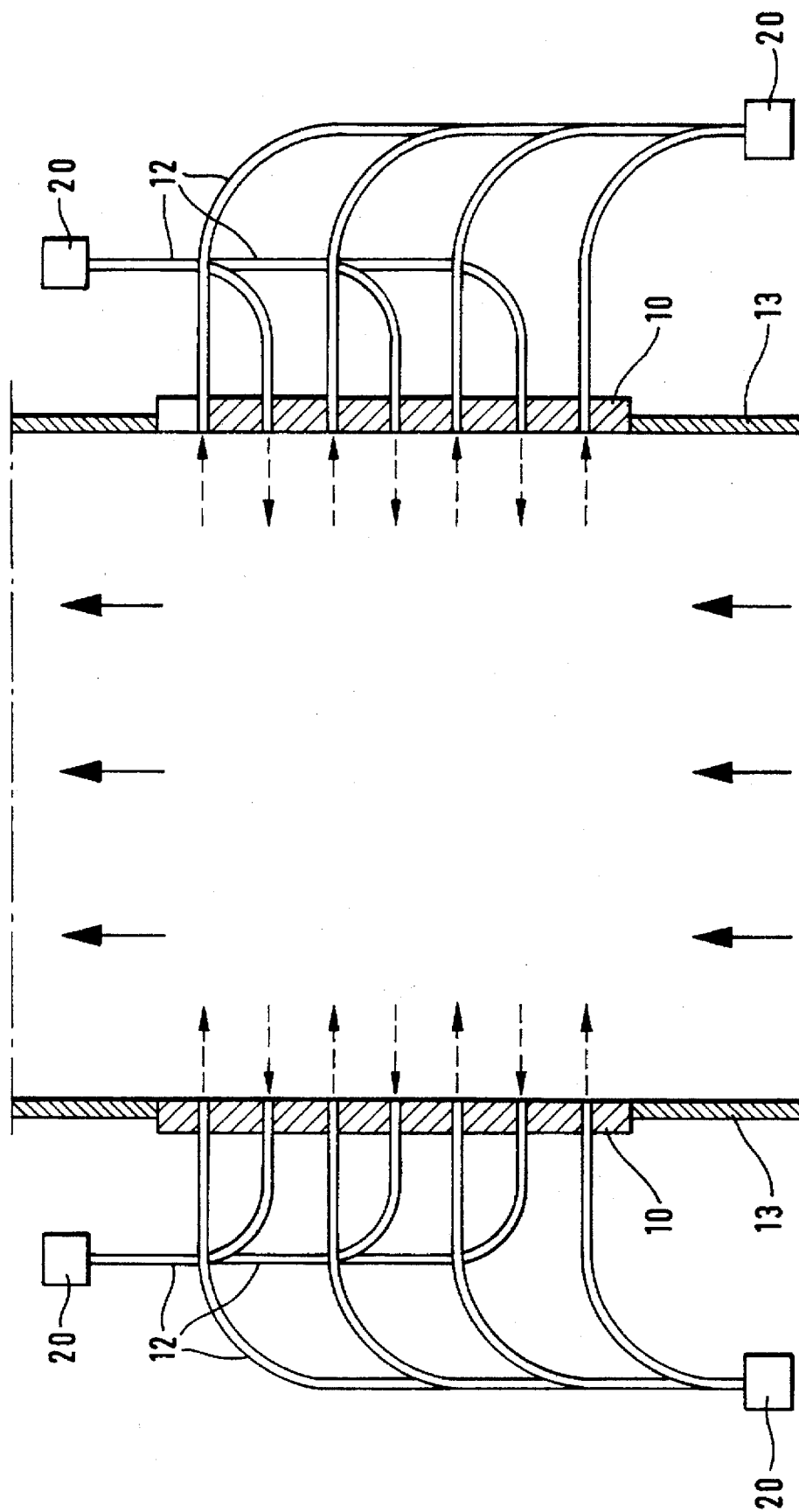

OPTICAL SPACE MONITORING APPARATUS COMPRISING LIGHT GUIDING FIBERS TRANSMITTING LIGHT THROUGH THE SPACE TO BE MONITORED

The present invention relates to an optical monitoring apparatus based on light transmission via light guide fibers or glass fibers.

BACKGROUND OF THE INVENTION

It is known to form an image of a cross section of a flowing fluid by means of a camera, the image being captured by an optical element serving spectral dispersion, and to process the radiation so spectrally dispersed by means of a sensor array read out serially. That is, the image of the fluid cross section is "one-dimensional" or line-shaped, the inlet aperture of the camera having a slot-like shape.

It is an object of the present invention to provide an apparatus for optically monitoring a space and which is of simple design.

It is a further object of the invention to provide such an apparatus that is also adapted to determine the distribution of radiation emanating from or absorbed by a flowing fluid in a flue of a steam generator, the resolution requirements being moderate.

SUMMARY OF THE INVENTION

According to the invention, radiation is detected at inlets of glass fibers or other light guide fibers, these inlets being disposed in an array for the purpose of monitoring a space (as contrasted to a cross section). The light guide fibers are not extended to a light sensor array of similar disposition (which would be obvious) but to at least one sensor row. This disposition permits parallel read-out of the information in real time and thus the detection of fluctuations. It is not feasible to detect such fluctuations by means of a sensor array because the latter is serially read out and, accordingly, inherently has integrating behavior.

At the inlet and/or outlet of each fiber, additional optical elements may be provided, such as microlenses, filters, prisms and the like, depending on the particular application.

Embodiments of the invention are schematically illustrated in the attached drawings.

BRIEF DESCRIPTION OF THE DRAWINGS

FIG. 6 is a section view of the modified apparatus of FIG. 5.

DETAILED DESCRIPTION OF THE INVENTION AND PREFERRED EMBODIMENTS

Figure 1:
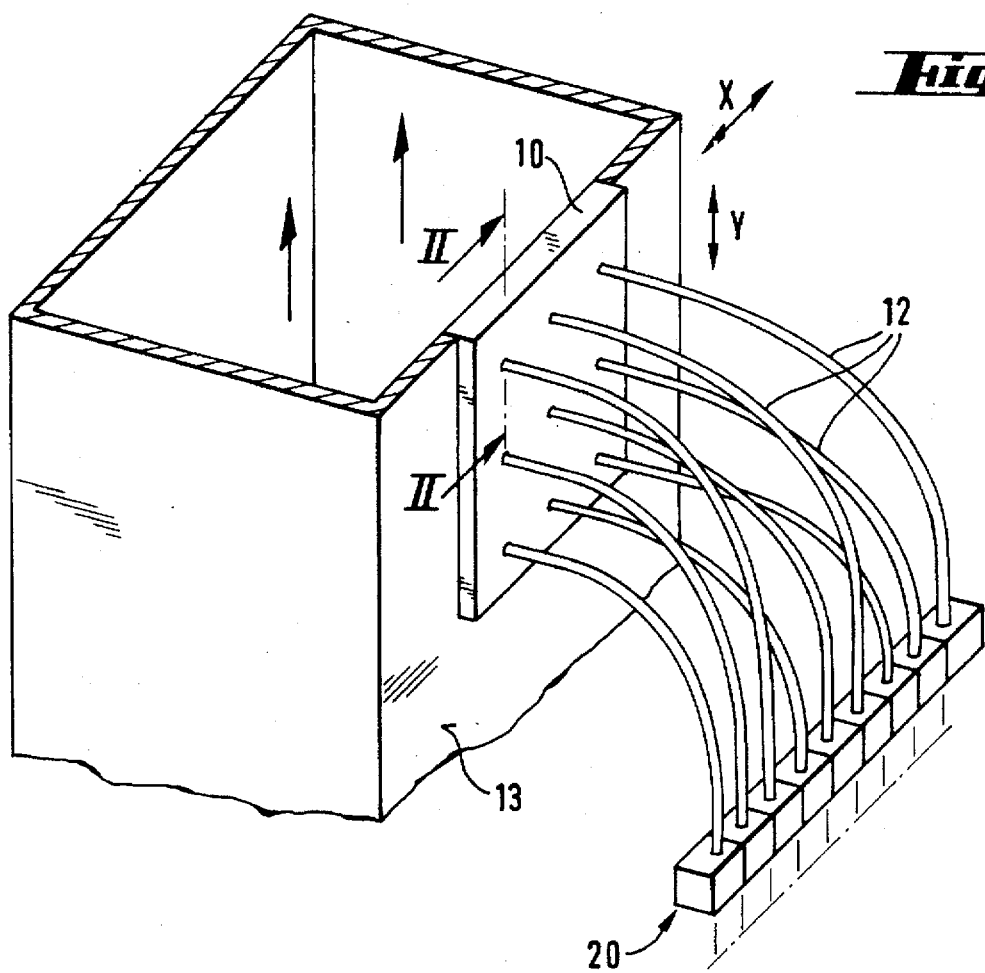
FIG. 1 shows an apparatus according to the invention for the detection of radiation fluctuations.

FIG. 1 shows a support 10 for nine glass fibers 12. The light inlets of the fibers are arranged in an orthogonal 3×3 array. It will be understood that the number of fibers will depend on the particular application and in general will be much higher than nine. A coordinate pair X, Y is associated with each light inlet. The light guiding fibers 12 are connected to a sensor row 20 wherein one sensor is allocated to each light guide. The sensors are read out in parallel, and processing of their output signals is done in an electronic processor, not shown.

Support 10 is mounted in a window provided in one of the walls 13 of a flue duct of a steam generator.

Figure 2:
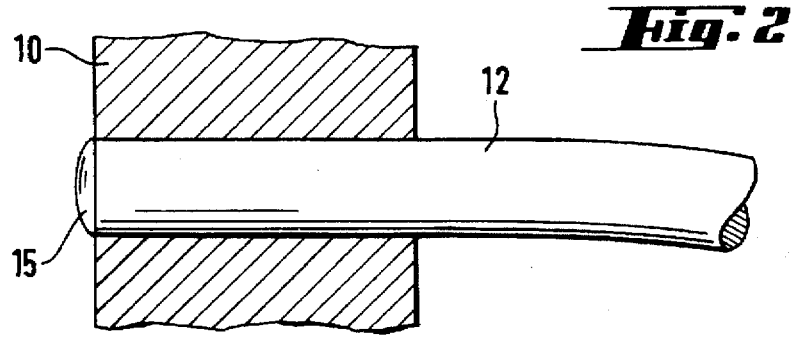
FIG. 2 shows a detail of the light inlet in FIG. 1 as indicated by II—II, in an enlarged scale.
Figure 3:
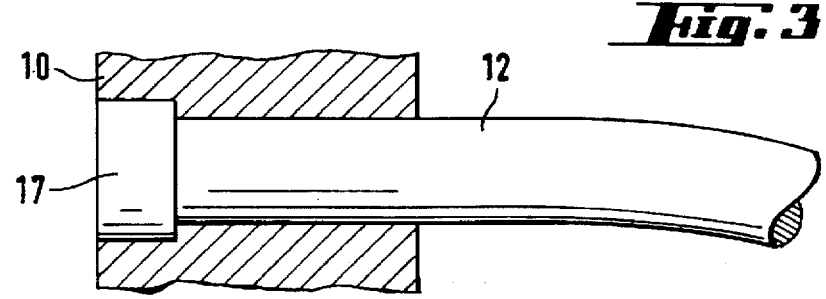
FIG. 3 is a view similar to FIG. 2 but with a modification.

The light inlets of fibers 12 may be provided with microlenses 15, as illustrated in FIG. 2, or with filter or other optical means 17, as illustrated in FIG. 3.

Figure 4:
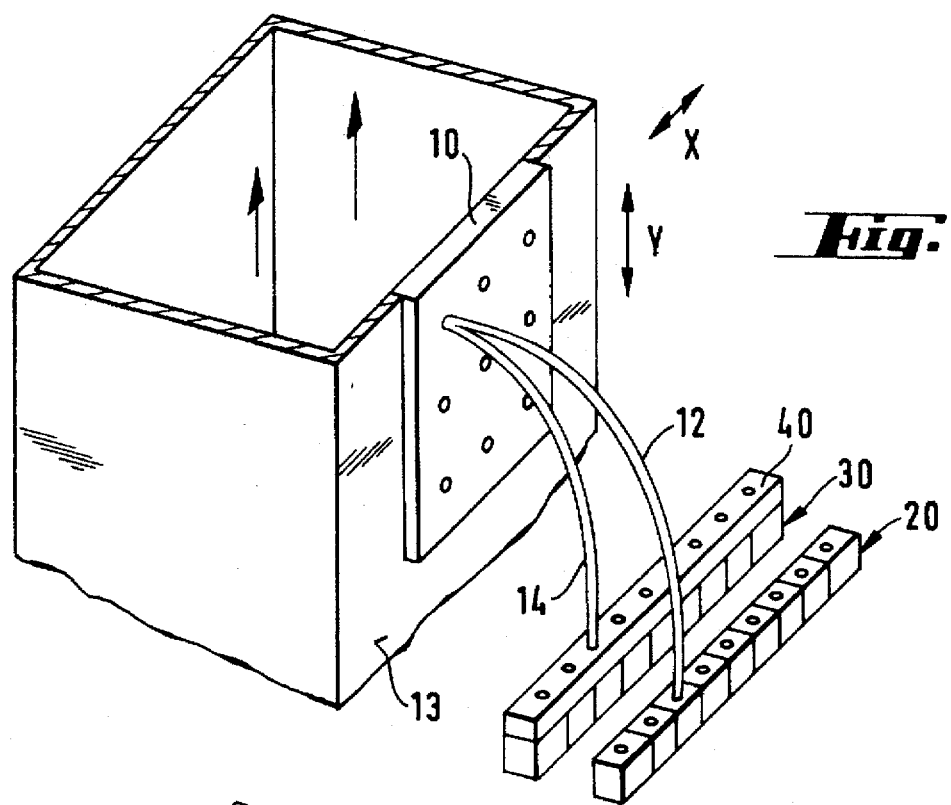
FIG. 4 shows an apparatus according to the invention for simultaneous detection of radiation fluctuations and radiation intensity in a given spectral wavelength range.

In the embodiment of FIG. 4, a pair of glass fibers 12, 14 is allocated to each site X, Y; for the sake of simplicity, only one such fiber pair is shown. Similar to FIG. 1, light guide fiber 12 is connected to the allocated sensor in the sensor row 20. The second fiber 14 of the pair is connected to an allocated sensor in a second sensor row 30, but between its light outlet and the sensor an optical element 40 for spectral dispersion is disposed so that only a desired section of the spectrum hits the sensor. This optical element may be of a known type, such as a prism, a filter, a diffraction gap or the like. The invention is not limited to only two rows; instead of two light guides per coordinate point, three or more may be provided in order to detect a plurality of spectral sections by means of a third, fourth, etc., sensor row. Also, instead of a second sensor row, a sensor array may be provided which will then be read out serially.

Figure 5:
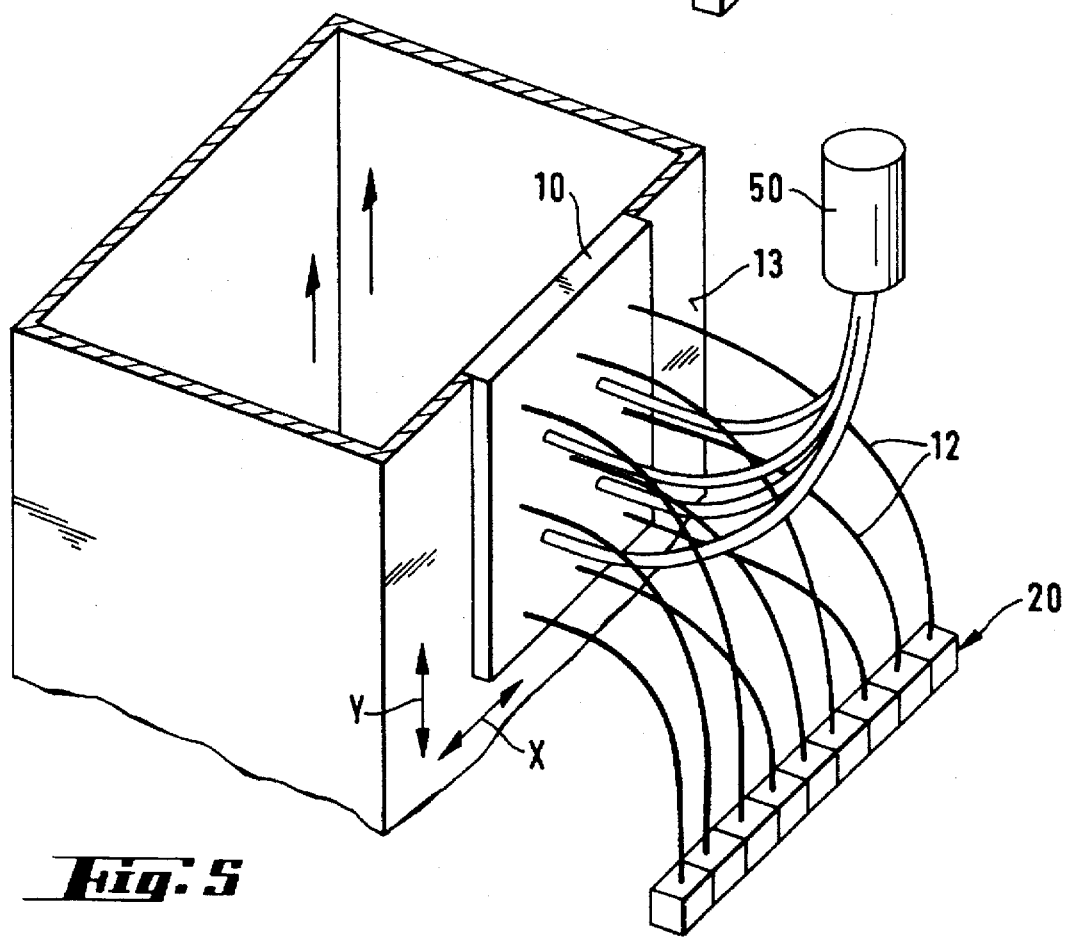
FIG. 5 illustrates a modification of the apparatus of FIG. 1.

In the embodiment of FIGS. 5 and 6, the apparatus comprises a light transmitter end and a light receiver end. At the transmitter end, the sensor rows are replaced with rows of light emitting diodes so that the light is not received at the array but emitted, the light source 50 being indicated as a block. At the receiver end, the system of FIG. 1 is used. In this manner, instead of radiation emanating from the flue gas its absorption of the laser output is detected.

As illustrated in FIG. 6, opposite transmitter/receiver ends may be provided wherein the light inlet of a receiver fiber captures the light emitted by the opposite light outlet and attenuated because of absorption. As shown, transmitters and receivers are provided at both sides.

We claim:

1. An optical space monitoring apparatus comprising a first set of light guiding fibers and a second set of light guiding fibers, each light guiding fiber having a light inlet and a light outlet, the light inlets of said first and second sets of light guiding fibers being arranged in a common array, the light outlets of said first set of light guiding fibers being connected to a first light sensor row, and the light outlets of said second set of light guiding fibers being connected to a second light sensor row with an optical dispersion element being disposed between said second fiber light outlets and the associated light sensor row, and the sensors of said first and second light sensor rows being read out in parallel.

2. An optical space monitoring apparatus disposed on a flue gas channel defined by a first wall portion and a second wall portion opposite said first wall portion, the apparatus comprising a first set of light guiding fibers having a light inlet and a light outlet, a second set of light guiding fibers having a light inlet and a light outlet, a third set of light guiding fibers having a light inlet and a light outlet, a fourth set of light guiding fibers having a light inlet and a light outlet, the light inlets of said first and third sets being connected to light source means, the light inlets of said second set being mounted in an array configuration in said first wall portion, the light inlets of said fourth set being mounted in an array configuration in said second wall portion, the light outlets of said first set being mounted in said first wall portion opposite the light inlets of said fourth set, the light outlets of said third set being mounted in said second wall portion opposite the light inlets of said second set, the light outlets of said second set being connected to a first light sensor row, the light outlets of said fourth set being connected to a second light sensor row, the sensors of said first and second light sensor rows being read out in parallel.

* * * * *